US010577298B2

(12) United States Patent
Flachsmann et al.

(10) Patent No.: US 10,577,298 B2
(45) Date of Patent: Mar. 3, 2020

(54) ARYL BETA DIKETONES AND THEIR USE AS ODORANTS

(71) Applicant: Givaudan SA, Vernier (CH)

(72) Inventors: Felix Flachsmann, Duebendorf (CH); Jean-Pierre Bachmann, Waedenswil (CH)

(73) Assignee: GIVAUDAN S.A., Vernier (CH)

(*) Notice: Subject to any disclaimer, the term of this patent is extended or adjusted under 35 U.S.C. 154(b) by 0 days.

(21) Appl. No.: 16/094,926

(22) PCT Filed: Apr. 27, 2017

(86) PCT No.: PCT/EP2017/060051
§ 371 (c)(1),
(2) Date: Oct. 19, 2018

(87) PCT Pub. No.: WO2017/186846
PCT Pub. Date: Nov. 2, 2017

(65) Prior Publication Data
US 2019/0127305 A1    May 2, 2019

(30) Foreign Application Priority Data
Apr. 28, 2016  (GB) .................... 1607404.9

(51) Int. Cl.
| | | |
|---|---|---|
| C07C 45/00 | (2006.01) | |
| C07C 49/00 | (2006.01) | |
| C07D 211/08 | (2006.01) | |
| A61K 8/00 | (2006.01) | |
| A61Q 19/00 | (2006.01) | |
| C07C 49/255 | (2006.01) | |
| C07C 49/185 | (2006.01) | |
| C07C 49/217 | (2006.01) | |
| C11B 9/00 | (2006.01) | |
| A61K 8/35 | (2006.01) | |
| C07D 317/46 | (2006.01) | |

(Continued)

(52) U.S. Cl.
CPC .............. *C07C 49/255* (2013.01); *A61K 8/35* (2013.01); *A61K 8/41* (2013.01); *A61Q 13/00* (2013.01); *C07C 49/185* (2013.01); *C07C 49/213* (2013.01); *C07C 49/217* (2013.01); *C07C 49/245* (2013.01); *C07C 49/248* (2013.01); *C07C 49/76* (2013.01); *C07D 207/06* (2013.01); *C07D 211/08* (2013.01); *C07D 317/46* (2013.01); *C11B 9/0061* (2013.01); *A61K 2800/57* (2013.01); *A61Q 19/10* (2013.01); *C07C 45/562* (2013.01); *C07C 45/61* (2013.01)

(58) Field of Classification Search
CPC ... C07C 45/562; C07C 49/255; C07C 49/185; C07C 49/76; C07D 211/08; A61K 8/35; A61K 8/41; A61Q 19/10
See application file for complete search history.

(56) References Cited

U.S. PATENT DOCUMENTS

| | | |
|---|---|---|
| 3,281,493 A | 10/1966 | Thornton et al. |
| 3,595,878 A | 7/1971 | Lee |

FOREIGN PATENT DOCUMENTS

| | | |
|---|---|---|
| CN | 101696228 A | 4/2010 |
| WO | WO 2015124671 A1 | 8/2015 |

OTHER PUBLICATIONS

PCT/EP2017/060051—International Search Report, dated Jun. 6, 2017.
PCT/EP2017/060051—International Written Opinion, dated Jun. 6, 2017.
GB1607404.9—Great Britain Search Report, dated Feb. 10, 2017.
Manfred Schlosser, et al. "About the "Physiological Size" of Fluorine Substituents: Comparison of Sensorially Active Compounds with Fluorine and Methyl Substituted Analogues" Tetrahedron, vol. 52, No. 1, pp. 99-108, 1996.

(Continued)

*Primary Examiner* — Sikarl A Witherspoon
(74) *Attorney, Agent, or Firm* — Curatolo Sidoti Co., LPA; Joseph G. Curatolo; Salvatore A. Sidoti

(57) ABSTRACT

The present invention refers to aryl beta diketones of the formula (I)

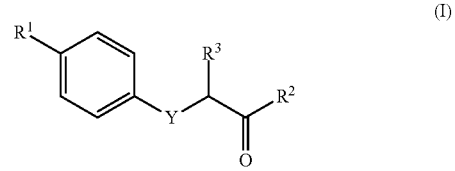

wherein Y, $R^1$, $R^2$ and $R^3$ have the meaning
$R^1$ is selected from the group consisting of hydrogen, $C_1$-$C_4$ alkyl, hydroxyl, methoxy, $CF_3$ and F;
$R^2$ is selected from the group consisting of methyl and ethyl;
$R^3$ is selected from the group consisting of methyl and ethyl; and
Y is a bivalent residue selected from the group consisting of —C(O)—; —CH$_2$—CH$_2$—C(O)—; —CR$^I$R$^{II}$—C(O)—, wherein R$^I$ and R$^{II}$ are independently selected from hydrogen and methyl; and —CHR$^{III}$—CHR$^{IV}$—C(O)—, wherein R$^{III}$ and R$^{IV}$ are independently selected from hydrogen and methyl with the proviso, that R$^{III}$=R$^{IV}$ are hydrogen or either R$^{III}$ or R$^{IV}$ is methyl. The invention further refers to fragrance compositions and fragranced articles comprising them.

11 Claims, No Drawings

(51) Int. Cl.
  *C07C 49/76* (2006.01)
  *A61Q 13/00* (2006.01)
  *C07C 49/213* (2006.01)
  *A61K 8/41* (2006.01)
  *C07C 49/245* (2006.01)
  *C07C 49/248* (2006.01)
  *C07D 207/06* (2006.01)
  *A61Q 19/10* (2006.01)
  *C07C 45/56* (2006.01)
  *C07C 45/61* (2006.01)

(56) References Cited

OTHER PUBLICATIONS

Benjamin Prek, et al. "Reactions of enaminones and related compounds with N,N-dimethylacetamide dimethyl acetal. A simple one-pot metal-free synthesis of polysubstituted benzene derivatives" Tetrahedron, 2014, vol. 70, No. 14, pp. 2359-2369.

Isao Kuwajima, et al. "a-Chloroacyltrimethylsilanes as a-Trimethylsilylacyl Equivalents. Specific C-Acylation of Enolates" Tetrahedron Letters No. 42, pp. 4095-4098, 1979.

A. Corsaro, et al., "Study of the Eschenmoser Sulfide Contraction Method With and Without a Thiophile" Phosphorus, Sulfur, and Silicon, 1992, vol. 71, No. 1-4, pp. 197-206.

Daniel Lim, et al., "MgBr$_2$·OEt$_2$-Promoted Coupling of Ketones and Activated Acyl Donors via Soft Enolization: A Practical Synthesis of 1,3-Diketones" Practical Synthetic Procedures, vol. 2008, No. 13 pp. 2148-2152.

John B. Paine, III, et al., "Regioselectivity of Pyrrole Synthesis from Diethyl Aminomalonate and 1,3-Diketones: Further Observations" J. Org. Chem 1987, vol. 52, No. 18, 3986-3993.

Yoshitaka Hamashima, et al., Catalytic Enantioselective Michael Reaction of 1,3-Dicarbonyl Compounds via Formation of Chiral Palladium Enolate Adv. Synth. & Catal. 2005, vol. 347, No. 11-13, 1576-1586.

Sato, et al. "Direct Syntheses of 1,3-Diketones by Rh-Catalyzed Reductive a-Acylation of Enones" Organic Letters, vol. 10 (12), May 14, 2008, pp. 2405-2408.

Gogsig, et al., "Palladium-Catalyzed Carbonylative—Arylation for Accessing 1,3-Diketones" Angewandte Chemie, International Edition, vol. 51 (3), 2012, pp. 798-801.

Ryan, et al. "Über ungesättigte β-Diketone. II" Chemisches Zentralblatt, Ausgabe Weinheim Verlag Chemie, DE vol. 84, No. 4, pp. 2040-2041. (1913).

ARYL BETA DIKETONES AND THEIR USE AS ODORANTS

CROSS REFERENCE TO RELATED APPLICATIONS

This application is a national stage application of International Application No. PCT/EP2017/060051, filed 27 Apr. 2017, which claims priority from Great Britain Patent Application No. 1607404.9, filed 28 Apr. 2016, which applications are incorporated herein by reference.

The present invention refers to aryl beta diketones and their use as odorants. This invention relates furthermore to a method of their production and fragrance compositions comprising them.

In the flavor and fragrance industry there is a constant demand for new compounds that enhance, modify or improve on odor notes. Surprisingly, it has been found that aryl beta diketones as defined by formula (I) herein below constitute, buttery, creamy odor notes which are accompanied by tea, floral, and/or fruity aspects and which are long lasting and providing a good substantivity.

Thus there is provided in a first embodiment the use as flavour or fragrance of a compound of formula (I)

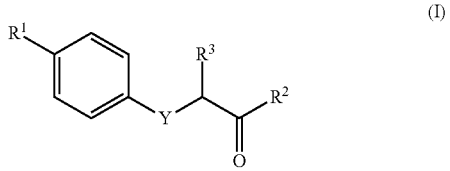

(I)

wherein
$R^1$ is selected from the group consisting of hydrogen, $C_1$-$C_4$ alkyl (methyl, ethyl, propyl, isopropyl, n-butyl, isobutyl, tertbutyl, 1-methyl-prop-1-yl), hydroxyl, methoxy, $CF_3$ and F;
$R^2$ is selected from the group consisting of methyl and ethyl;
$R^3$ is selected from the group consisting of methyl and ethyl; and
Y is a bivalent residue selected from the group consisting of
—C(O)—; —CH$_2$=CH$_2$—C(O)—; —CR$^I$R$^{II}$—C(O)—, wherein $R^I$ and $R^{II}$ are independently selected from hydrogen and methyl; and —CHR$^{III}$—CHR$^{IV}$—C(O)—, wherein $R^{III}$ and $R^{IV}$ are independently selected from hydrogen and methyl with the proviso that $R^{III}$=$R^{IV}$ are hydrogen or either $R^{III}$ or $R^{IV}$ is methyl.

Non-limiting examples are compounds of formula (I) wherein $R^1$ is hydrogen, methyl, methoxy or hydroxyl.

Further, non-limiting examples are compounds of formula (I) wherein $R^2$ and $R^3$ are methyl.

Further, non-limiting examples are compounds of formula (I) wherein Y is a bivalent residue selected from the group consisting of —C(O)—; —CH$_2$—C(O)—; and —CH$_2$—CH$_2$—C(O)—.

Further, non-limiting examples are compounds of formula (I) wherein $R^1$ is selected from hydrogen, methyl, methoxy and hydroxyl, and $R^2$ and $R^3$ are methyl.

Further, non-limiting examples are compounds of formula (I) wherein $R^2$ and $R^3$ are methyl and Y is a bivalent residue selected from the group consisting of —C(O)— and —CH$_2$—C(O)—.

Further, non-limiting examples are compounds of formula (I) wherein $R^1$ is not hydrogen, $R^2$ is methyl, and $R^3$ is selected from methyl and ethyl.

Further, non-limiting examples are compounds of formula (I) wherein $R^1$ is hydrogen, methyl, methoxy or hydroxyl, and $R^2$ and $R^3$ are methyl.

Further, non limiting examples are compounds of formula (I) wherein $R^1$ is hydrogen, methyl, or methoxy, $R^2$ and $R^3$ are methyl, and Y is a bivalent residue selected from the group consisting of —C(O)—; —CH$_2$C(O)—; and —CH$_2$—CH$_2$—C(O)—.

Further, none-limiting examples are compounds of formula (I) comprising 10 to 15 (including 11, 12, 13, and 14) carbon atoms.

As a specific example of compounds of formula (I), one may cite, as non-limiting example, 2-methyl-1-(p-tolyl)butane-1,3-dione, which possesses a distinct floral creamy, buttery, jasmine, anisic, black tea connotations.

As a further specific example of compounds of formula (I), one may cite, as non-limiting example, 6-(4-methoxyphenyl)-3-methylhexane-2,4-dione, which possesses a distinct buttery, fruity, raspberry, liquorice connotations.

Further, non-limiting examples are compounds of formula (I) selected from the group consisting of 2-methyl-1-phenylbutane-1,3-dione,
3-methyl-1-phenylbutane-2,4-dione,
3-methyl-6-phenylhexane-2,4-dione,
3-methyl-6-phenylhex-5-ene-2,4-dione,
1-(4-methoxyphenyl)-2-methylbutane-1,3-dione,
6-(4-hydroxyphenyl)-3-methylhexane-2,4-dione,
2-ethyl-1-(p-tolyl)butane-1,3-dione,
1-(4-ethylphenyl)-2-methylbutane-1,3-dione,
2-methyl-1-(4-(trifluoromethyl)phenyl)butane-1,3-dione, and
2-methyl-1-(p-tolyl)pentane-1,3-dione.

Surprisingly inventors found that the substituent $R^3$ is highly relevant with regard to the odor character and the odor threshold of the compounds of formula (I). Compounds of formula (I) wherein $R^3$ is hydrogen, the buttery odor note is missing. Furthermore it was observed that they possess a higher odor threshold compared to their equivalents wherein $R^3$ is methyl or ethyl.

1,3-Diketones of formula (I) exist in equilibrium with their so-called tautomeric structures, which comprise two possible regioisomers (Ia, and Ib), depending on which of the keto groups undergoes enolization.

More particular the tautomers of compounds of formula (I) are compounds of formula (Ia) and (Ib)

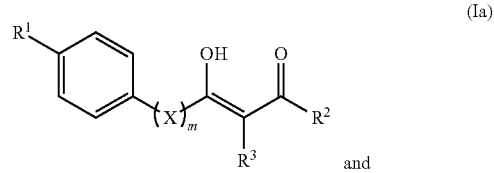

(Ia)

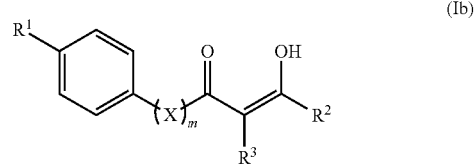

(Ib)

wherein

R$^1$, R$^2$, and R$^3$ have the same meaning as defined for compounds of formula (I), m is 0 or 1; and X is a bivalent residue selected from the group consisting of —CH$_2$=CH$_2$—; —CR$^I$R$^{II}$, wherein R$^I$ and R$^{II}$ are independently selected from hydrogen and methyl; and —CHR$^{III}$—CHR$^{IV}$—, wherein R$^{III}$ and R$^{IV}$ are independently selected from hydrogen and methyl with the proviso that R$^{III}$=R$^{IV}$ are hydrogen or either R$^{III}$ or R$^{IV}$ is methyl.

Each regioisomeric tautomeric structure (Ia and Ib) can be formed as E- and Z-isomers, with the preference for the Z-isomer, in which an intramolecular hydrogen bond can be formed between the enol-OH group and the keto group. The relative amounts of 1,3-diketone of formula (I) versus its respective tautomeric hydroxy enone (Ia; Ib) depend on solvent and pH.

Detailed analytical analysis has shown that the compounds of formula (I) may autoxidate during storage resulting in mixtures comprising compounds of formula (I) and traces of compounds of formula (Ic)

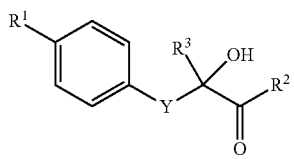

(Ic)

wherein R$^1$, R$^2$, R$^3$ and Y have the same meaning as defined for compounds of formula (I), which may have certain impact on the overall olfactive profile.

The compound of formula (I) may be used alone, or in combination with a base material. As used herein, the 'base material' includes all known odorant molecules selected from the extensive range of natural products, and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, and other auxiliary agents commonly used in the art.

The term "auxiliary agent" refers to ingredients that might be employed in a fragrance composition for reasons not specifically related to the olfactive performance of said composition. For example, an auxiliary agent may be an ingredient that acts as an aid to processing a fragrance ingredient or ingredients, or a composition containing said ingredient(s), or it may improve handling or storage of a fragrance ingredient or composition containing same. It might also be an ingredient that provides additional benefits such as imparting color or texture. It might also be an ingredient that imparts light resistance or chemical stability to one or more ingredients contained in a fragrance composition. A detailed description of the nature and type of adjuvants commonly used in fragrance compositions containing same cannot be exhaustive, but it has to be mentioned that said ingredients are well known to a person skilled in the art.

As used herein, 'fragrance composition' means any composition comprising the compound of formula (I) and a base material, e.g. a diluent conventionally used in conjunction with odorants, such as diethyl phthalate (DEP), dipropylene glycol (DPG), isopropyl myristate (IPM), triethyl citrate (TEC) and alcohol (e.g. ethanol). Optionally, the composition may comprise an anti-oxidant adjuvant. Said anti-oxidant may be selected from Tinogard® TT (BASF), Tinogard® Q (BASF), Tocopherol (including its isomers, CAS 59-02-9; 364-49-8; 18920-62-2; 121854-78-2), 2,6-bis (1,1-dimethylethyl)-4-methylphenol (BHT, CAS 128-37-0) and related phenols, hydroquinones (CAS 121-31-9). To avoid the release of diacetyl under certain conditions 100-1000 ppm of an anti-oxidant may be added.

The following list comprises examples of known odorant molecules, which may be combined with the compound of the present invention:

essential oils and extracts, e.g. castoreum, costus root oil, oak moss absolute, geranium oil, tree moss absolute, basil oil, fruit oils, such as bergamot oil and mandarine oil, myrtle oil, palmarose oil, patchouli oil, petitgrain oil, jasmine oil, rose oil, sandalwood oil, wormwood oil, lavender oil and/or ylang-ylang oil;

alcohols, e.g. cinnamic alcohol ((E)-3-phenylprop-2-en-1-ol); cis-3-hexenol ((Z)-hex-3-en-1-ol); citronellol (3,7-dimethyloct-6-en-1-ol); dihydro myrcenol (2,6-dimethyloct-7-en-2-ol); Ebanol™ ((E)-3-methyl-5-(2,2,3-trimethylcyclopent-3-en-1-yl)pent-4-en-2-ol); eugenol (4-allyl-2-methoxyphenol); ethyl linalool ((E)-3,7-dimethylnona-1,6-dien-3-ol); farnesol ((2E,6Z)-3,7,11-trimethyldodeca-2,6,10-trien-1-ol); geraniol ((E)-3,7-dimethylocta-2,6-dien-1-ol); Super Muguet™ ((E)-6-ethyl-3-methyloct-6-en-1-ol); linalool (3,7-dimethylocta-1,6-dien-3-ol); menthol (2-isopropyl-5-methylcyclohexanol); Nerol (3,7-dimethyl-2,6-octadien-1-ol); phenyl ethyl alcohol (2-phenylethanol); Rhodinol™ (3,7-dimethyloct-6-en-1-ol); Sandalore™ (3-methyl-5-(2,2,3-trimethylcyclopent-3-en-1-yl)pentan-2-ol); terpineol (2-(4-methylcyclohex-3-en-1-yl) propan-2-ol); or Timberol™ (1-(2,2,6-trimethylcyclohexyl)hexan-3-ol); 2,4,7-trimethylocta-2,6-dien-1-ol, and/or [1-methyl-2(5-methylhex-4-en-2-yl)cyclopropyl]-methanol;

aldehydes and ketones, e.g. anisaldehyde (4-methoxybenzaldehyde); alpha amyl cinnamic aldehyde (2-benzylideneheptanal); Georgywood™ (1-(1,2,8,8-tetramethyl-1,2,3,4,5,6,7,8-octahydronaphthalen-2-yl) ethanone); Hydroxycitronellal (7-hydroxy-3,7-dimethyloctanal); Iso E Super® (1-(2,3,8,8-tetramethyl-1,2,3,4,5,6,7,8-octahydronaphthalen-2-yhethanone); Isoraldeine® ((E)-3-methyl-4-(2,6,6-trimethylcyclohex-2-en-1-yl)but-3-en-2-one); Hedione® (methyl 3-oxo-2-pentylcyclopentaneacetate); 3-(4-isobutyl-2-methylphenyl)propanal; maltol; methyl cedryl ketone; methylionone; verbenone; and/or vanillin;

ether and acetals, e.g. Ambrox® (3a,6,6,9a-tetramethyl-2,4,5,5a,7,8,9,9b-octahydro-1H-benzo[e][1]benzofuran); geranyl methyl ether ((2E)-1-methoxy-3,7-dimethylocta-2,6-diene); rose oxide (4-methyl-2-(2-methylprop-1-en-1-yl)tetrahydro-2H-pyran); and/or Spirambrene® (2',2',3,7,7-pentamethylspiro[bicyclo [4.1.0]heptane-2,5'-[1,3]dioxane]);

esters and lactones, e.g. benzyl acetate; cedryl acetate ((1S,6R,8aR)-1,4,4,6-tetramethyloctahydro-1H-5,8a-methanoazulen-6-yl acetate); γ-decalactone (6-pentyltetrahydro-2H-pyran-2-one); Helvetolide® (2-(1-(3,3-dimethylcyclohexyl)ethoxy)-2-methylpropyl propionate); γ-undecalactone (5-heptyloxolan-2-one);

and/or vetiveryl acetate ((4,8-dimethyl-2-propan-2-ylidene-3,3a,4,5,6,8a-hexahydro-1H-azulen-6-yl) acetate);

macrocycles, e.g. Ambrettolide ((Z)-oxacycloheptadec-10-en-2-one); ethylene brassylate (1,4-dioxacycloheptadecane-5,17-dione); and/or Exaltolide® (16-oxacyclohexadecan-1-one); and heterocycles, e.g. isobutylquinoline (2-isobutylquinoline).

In one specific embodiment the compounds of formula (I) (such as 2-methyl-1-(p-tolyhbutane-1,3-dione, and/or 6-(4-methoxyphenyl)-3-methylhexane-2,4-dione) may be admixed to floral fragrance compositions, resulting in fragrance compositions possessing more volume, with an enhanced floralcy compared to compositions free of compounds of formula (I). In addition, the admixture will add a soft creamy effect to the odor profile. Thus there is provided in a further aspect a fragrance composition comprising a compound of formula (I) as hereinabove defined and at least one additional odorant. In one embodiment the at least one additional odorant is an odorant having a floral odor note.

The compound according to formula (I) may be used in a broad range of fragranced articles, e.g. in any field of fine and functional perfumery, such as perfumes, air care products, household products, laundry products, body care products and cosmetics. The compound can be employed in widely varying amounts, depending upon the specific article and on the nature and quantity of other odorant ingredients. The proportion is typically from 0.0001 to 30 weight percent of the article. In one embodiment, the compound of the present invention may be employed in a fabric softener in an amount from 0.001 to 0.3 weight percent. In another embodiment, the compound of the present invention may be used in fine perfumery in amounts from 0.01 to 30 weight percent (e.g. up to about 10 or up to 20 weight percent), more preferably between 0.01 and 6 weight percent. However, these values are given only by way of example, since the experienced perfumer may also achieve effects or may create novel accords with lower or higher concentrations.

The compound as described hereinabove may be employed in a consumer product base simply by directly mixing the compound of formula (I), or a fragrance composition with the consumer product base, or it may, in an earlier step, be entrapped with an entrapment material, for example, polymers, capsules, microcapsules and nanocapsules, liposomes, film formers, absorbents such as carbon or zeolites, cyclic oligosaccharides and mixtures thereof.

In a further embodiment, the compound of formula (I) may be chemically bonded to substrates, which are adapted to generate the fragrance molecule upon application of an external stimulus such as light, enzyme, oxygen, or the like, and then mixed with the consumer product base. This is particularly useful in some applications, such as laundry or hair care, as the compound can be generated in situ, when its presence is desired.

There is therefore also provided a precursor capable of generating a compound of the formula (I), the precursor being a compound of the formula (II)

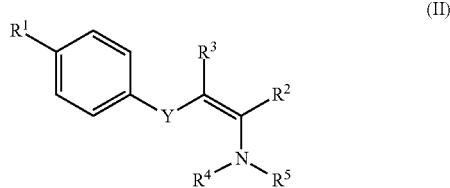

(II)

wherein Y, $R^1$ $R^2$ and $R^3$ have the same meaning as for formula (I); and in which $R^4$ and $R^5$ are selected independently from linear or branched $C_1$-$C_{15}$ alkyl, aryl, and $C_3$-$C_8$ cycloalkyl, the cycloalkyl and aryl being optionally substituted with linear or branched $C_1$-$C_7$ alkyl groups; or $R^4$ and $R^5$ may, together with the nitrogen atom to which they are attached, form a 5- or 6-membered ring, e.g. a pyrrolidine or a piperidine: or $R^4$ and $R^5$, together with the nitrogen atom to which they are attached, form part of a polymeric entity.

In the case of polymeric entities, any such suitable entity is suitable, a typical example being a polyethylene imine. Such materials are readily available commercially, for example the Lupasol™ range of BASF.

There is therefore also provided a method of providing in a fragranced article a compound of formula (I) as hereinabove described, comprising
(i) the preparation of a compound of formula (II)
(ii) adding the compound of formula (II) to an application; and
(iii) subjecting the application to conditions that will result in the generation of a compound of the formula (I).

There is further provided the use of a compound of formula (II) in a fragranced article for the in situ generation of a compound according to formula (I).

Although compounds of the general type of formula (II) are known (e.g. U.S. Pat. No. 4,226,892), it was not known that a particular subset of this group has this particular advantage.

The compound of formula (II) may be prepared by any suitable method known to the person skilled in the art. The materials and conditions for such a preparation are well known to the art, and only routine, non-inventive experimentation is required to produce a suitable compound. In a typical, non-limiting example, a compound of formula (II) may be prepared by the reaction of approximately equimolar amounts of a compound of formula (I) with one of $HNR^4R^5$, preferably at 20-160° C., either neat or in a solvent such as toluene or cyclohexane, preferably in the presence of an acid catalyst, such as p-toluene sulfonic acid, preferably under continuous removal of water, e.g. by using toluene as the solvent at reflux temperature and with a Dean-Stark trap, or the use of a water binding additive, such as sodium sulfate. The product may be isolated by standard workup procedures known to the person skilled in the art of organic synthesis. The compound of formula (II) may be used in crude form, or it may be purified by standard purification procedures, such as column chromatography or distillation.

There is further provided a method of manufacturing a fragranced article, comprising the incorporation of a compound of formula (I) or its precursor (i.e. a compound of formula (II)), as a fragrance ingredient, either by directly admixing the compound to the consumer product base or by admixing a fragrance composition comprising the compound of formula (I) or its precursor (i.e. a compound of formula (II)), which may then be mixed with a consumer product base, using conventional techniques and methods. Through the addition of an olfactory acceptable amount of the compound of the present invention as hereinabove described the odor notes of a consumer product base will be improved, enhanced, or modified.

Thus, the invention furthermore provides a method for improving, enhancing or modifying a consumer product base by means of the addition thereto of an olfactorily acceptable amount of the compound of formula (I) or its precursor (i.e. a compound of formula (II)).

The invention also provides a fragranced article comprising:
a) as odorant the compound of formula (I), its precursor, or a mixture thereof; and
b) a consumer product base.

As used herein, 'consumer product base' means a composition for use as a consumer product to fulfil specific actions, such as cleaning, softening, and caring or the like. Examples of such products include fine perfumery, e.g. perfume and eau de toilette; fabric care, household products and personal care products such as cosmetics, laundry care detergents, rinse conditioner, personal cleansing composition, detergent for dishwasher, surface cleaner; laundry products, e.g. softener, bleach, detergent; body-care products, e.g. shampoo, shower gel; air care products (includes products that contain preferably volatile and usually pleasant-smelling compounds which advantageously can even in very small amounts mask unpleasant odors). Air fresheners for living areas contain, in particular, natural and synthetic essential oils such as pine needle oils, citrus oil, eucalyptus oil, lavender oil, and the like, in amounts for example of up to 50% by weight. As aerosols they tend to contain smaller amounts of such essential oils, by way of example less than 5% or less than 2% by weight, but additionally include compounds such as acetaldehyde (in particular, <0.5% by weight), isopropyl alcohol (in particular, <5% by weight), mineral oil (in particular, <5% by weight), and propellants.

Cosmetic products include:
(a) cosmetic skincare products, especially bath products, skin washing and cleansing products, skincare products, eye makeup, lip care products, nail care products, intimate care products, foot care products;
(b) cosmetic products with specific effects, especially sunscreens, tanning products, de-pigmenting products, deodorants, antiperspirants, hair removers, and shaving products;
(c) cosmetic dental-care products, especially dental and oral care products, tooth care products, cleaners for dental prostheses, adhesives for dental prostheses; and
(d) cosmetic hair care products, especially hair shampoos, hair care products, hair setting products, hair-shaping products, and hair coloring products.

This list of products is given by way of illustration, and is not to be regarded as being in any way limiting.

Inventors have observed, that the use of compounds of formula (I) as hereinabove defined in certain consumer product bases, especially in liquid consumer product basis with a pH>9, tend to release minor amounts of aryl ketones.

Thus, more preferred are consumer products with a pH of 9 and lower, such as shampoo, detergent, fabric conditioner, hair conditioner, liquid soap, bar soap, shower gel, tumble dryer sheet, body lotion, and skin care cream.

Whereas, according to our best knowledge, only very few compounds as such are known from the literature, other compounds falling within the definition of formula (I) as hereinabove defined are not described in the literature and are thus novel in their own right.

Thus, there is provided in a further aspect of the invention a compound of formula (I)

$R^1$ is selected from the group consisting of hydrogen, $C_1$-$C_4$ alkyl (methyl, ethyl, propyl, isopropyl, n-butyl, isobutyl, tertbutyl, 1-methyl-prop-1-yl), hydroxyl, methoxy, $CF_3$ and F;

$R^2$ is selected from the group consisting of methyl and ethyl;

$R^3$ is selected from the group consisting of methyl and ethyl; and

Y is a bivalent residue selected from the group consisting of —$CH_2$=$CH_2$—C(O)—, and —$CHR^{III}$—$CHR^{IV}$—C(O)—, wherein $R^{III}$ and $R^{IV}$ are independently selected from hydrogen and methyl with the proviso that $R^{III}$=$R^{IV}$ are hydrogen or either $R^{III}$ or $R^{IV}$ is methyl; 2-ethyl-1-(p-tolyl)butane-1,3-dione, and 2-methyl-1-(p-tolyl)pentane-1,3-dione.

The compounds of formula (I) may be prepared by methods known to the person skilled in the art. For examples, compounds of formula (I) wherein Y is —C(O)— may be prepared by a Claisen condensation between a ketone 15 and an acetate or or propionate 11, where $R^6$ is alkyl, for example, methyl, ethyl, isopropyl or t-butyl, resulting directly in one step to compounds of formula (I), as depicted in Scheme 1. An appropriate base is potassium t-butoxide and an appropriate solvent is tetrahydrofurane.

Scheme 1:

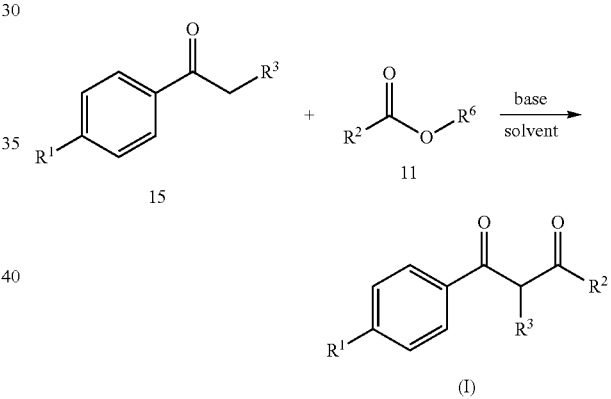

All other compounds of formula (I) as hereinabove defined, wherein Y is not —C(O)— may be prepared via a Claisen condensation between a methyl ketone 10 and an acetate or propionate 11 to provide intermediate diketone 12. Alternatively, the condensation can be carried out between an ester 13 and acetone. $R^6$ is, for example, methyl, ethyl, isopropyl or t-butyl. Suitable bases are for example sodium hydride, sodium ethoxide, potassium ethoxide, sodium t-butoxide or potassium t-butoxide. Suitable solvents are for example tetrahydrofurane or mixtures of toluene with 5-90% N-methyl pyrrolidone. The intermediate 12 is alkylated in Step B with an electrophile X—$R^3$, whereas X is, for example, iodide, i.e. X—$R^3$ is methyl iodide or ethyl iodide, in the presence of a base, such as lithium hydroxide hydrate or sodium hydride, and a solvent, such as tetrahydrofurane, resulting in compounds of formula (I), as depicted in Scheme 2. Suitable temperatures for steps A and B are 0-120° C., preferably 40-70° C. In order to avoid dialkylation, the method described by R. Antonioletti et al., *Gazetta Chimica Italiana* 1992, 122, 237-8, may be used.

Scheme 2:

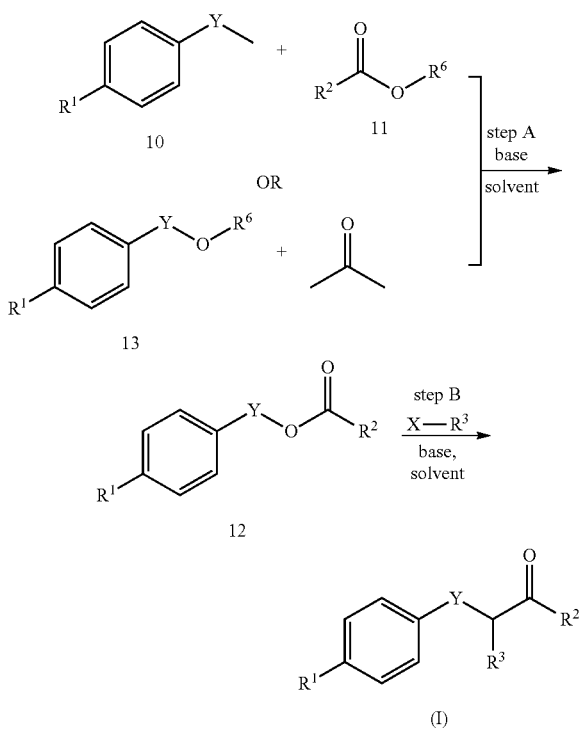

A special variant of the method depicted in Scheme 2 is the condensation of 13 with diethyl ketone yielding the product 14 directly, which corresponds to compounds of formula (I) with R³=methyl and R²=ethyl (Scheme 3). The choice of base, solvent and temperature is as described above.

Scheme 3:

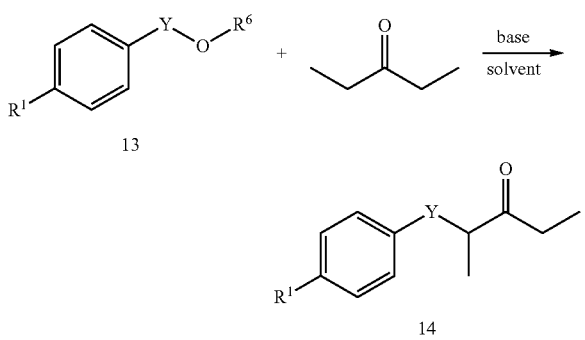

The invention is now further described with reference to the following non-limiting examples. These examples are for the purpose of illustration only, and it is understood that variations and modifications can be made by one skilled in the art.

EXAMPLE 1

2-methyl-1-(p-tolyl)butane-1,3-dione 1.1. 1-(p-tolyl)butane-1,3-dione

To the suspension of NaH (13.65 g of a 60% suspension in mineral oil, washed with hexane, 366 mmol, 1.1 equiv.) in toluene (210 ml) was added the solution of methyl 4-methylbenzoate (50.0 g, 333 mmol, 1 equiv) in N-methyl pyrrolidone (NMP, 100 ml) within 10 min at room temperature under intense stirring. The mixture was then warmed to 50° C. and the solution of acetone (27.1 g, 466 mmol, 1.4 equiv.) in toluene (100 ml) was added dropwise over 1 h (inside temperature ca. 45-55° C., gas evolution). After finished addition, the brown suspension was stirred at 50° C. for another 30 min, after which it was diluted with toluene (300 ml), stirred for 5 min at 50° C., then poored on a mixture of 2 N aqueous HCl solution (200 ml) and ice. The acidic aqueous layer was further extracted with toluene, and the combined organic layers were washed thoroughly three times with water (to extract most of the NMP), then dried over MgSO₄. The solvents were removed in a rotary evaporator under vacuum and the orange residue was diluted with hexane/toluene 7:2 (90 ml) and left to stand in refrigerator over night. The crystalline precipitate was separated by filtration (mainly p-methyl benzoic acid) and discarded. The filtrate was concentrated (37.6 g of clear orange oil) and distilled over a 10 cm Vigreux column at 104-105° C./0.02 mbar to isolate the olfactorily pure 1-(p-tolyl)butane-1,3-dione (clear, slightly yellow oil, 17.6 g, 65%).

Odor description: anisic, fennel seed, with connotations of p-cresol and myrrh.

The NMR-spectra indicate the presence of 83% enol and 17% diketo form.

$^1$H NMR (400 MHz, CDCl$_3$): 7.93-7.98 (m, 0.2H), 7.86 (d, J=8.3 Hz, 0.2H), 7.77-7.83 (m, 2H), 7.26 (dd, J=8.6, 0.7 Hz, 2.4H), 6.17 (s, 1H), 4.08 (s, 0.2H), 2.42 (s, 3.6H), 2.31 (s, 0.3H), 2.20 (s, 3.1H).

$^{13}$C NMR (101 MHz, CDCl$_3$): 202.5 (s), 193.4 (s), 193.0 (s), 183.7 (s), 143.0 (s), 132.1 (s), 129.4 (d), 129.3 (d), 128.9 (d), 128.7 (d), 127.0 (d), 96.2 (d), 54.6 (t), 30.5 (q), 25.6 (q), 21.5 (q).

1.2. 2-methyl-1-(p-tolyl)butane-1,3-dione

To the solution of 1-(p-tolyl)butane-1,3-dione (25.1 g, 142 mmol) in THF (141 ml) was added lithium hydroxide hydrate (5.98 g, 142 mmol, 1 equiv.), which dissolved completely after stirring at room temperature for 15 min. Then methyl iodide (30.3 g, 214 mmol, 1.5 equiv.) was added at once. The resulting clear orange solution was warmed to 50° C. and stirred for 7 h. It was transferred into a separatory funnel and diluted with toluene. The organic layer was washed with water, then 2 N aq. HCl solution (80 ml, 160 mmol), and brine (three times). All aqueous layers were extracted once with toluene. The combined organic layers were dried over MgSO₄, then the solvents were removed in a rotary evaporator under vacuum and the residue was purified by flash chromatography on silica gel with toluene/MTBE 29:1 to isolate the product as a clear, slightly yellow oil (21.6 g, 80%), which was further purified by distillation over a 10 cm Vigreux column at 90-110° C./0.02 mbar to isolate the olfactorily pure 2-methyl-1-(p-tolyl)butane-1,3-dione (clear, slightly yellow oil, 25.2 g, 43%).

The NMR-spectra indicate the presence of >95% diketo form.

$^1$H NMR (400 MHz, CDCl$_3$): 7.80-7.98 (m, 2H), 7.24-7.36 (m, 2H), 4.48 (q, J=7.0 Hz, 1H), 2.37-2.48 (m, 3H), 2.10-2.20 (m, 3H), 1.45 (d, J=6.9 Hz, 3H).

$^{13}$C NMR (101 MHz, CDCl$_3$): 205.1 (s), 196.9 (s), 144.7 (s), 133.4 (s), 129.5 (d), 128.8 (d), 56.7 (d), 27.8 (q), 21.6 (q), 13.6 (q).

Odor description: floral creamy, buttery, jasmine, anisic, black tea.

EXAMPLE 2

2-methyl-1-phenylbutane-1,3-dione

To the suspension of NaH (4.36 g of a 60% suspension in mineral oil, washed with hexane, 100 mmol, 1.0 equiv.) in tetrahydrofurane (THF, 25 ml) was added the solution of ethyl benzoate (15.0 g, 100 mmol, 1 equiv). The suspension was heated to 50° C. and under intense stirring the solution of acetone (6.97 g, 120 mmol, 1.2 equiv.) in THF (25 ml) was added dropwise over 2 h. This resulted in an exothermic reaction with gas evolution ($H_2$). The inside temperature was kept at 50-53° C. by temporarily removing the heating oil bath. The brownish suspension was stirred for additional 16 h at 50° C., then cooled to 10° C. and the solution of methyl iodide (15.61 g, 110 mmol, 1.1 equiv.) in THF (25 ml) was added dropwise over 30 min. The resulting beige suspension was stirred for additional 24 h at r.t., diluted with toluene and washed with water, sat. aq. $NaHCO_3$ solution and brine/water 1:1 (3 times). The organic layer was dried over $MgSO_4$ and the solvents were removed in a rotary evaporator under vacuum. The residual orange oil (10.2 g) was distilled first over a 10 cm Vigreux column at 80-90° C./0.06 mbar (7.2 g of a yellow oil), then over a 10 cm Widmer column at 92-93° C./0.05 mbar to yield the olfactorily pure 2-methyl-1-phenylbutane-1,3-dione (clear, slightly yellow oil, 4.4 g, 25%).

Odor description: floral, buttery, black tea, herbaceous, jasmone, minty, carvi, woody dry tobacco.

$^1$H NMR (400 MHz, $CDCl_3$): 7.86-8.04 (m, 2H), 7.52-7.60 (m, 1H), 7.41-7.50 (m, 2H), 4.48 (q, J=7.1 Hz, 1H), 2.13 (s, 3H), 1.41 (d, J=7.1 Hz, 3H).

$^{13}$C NMR (101 MHz, $CDCl_3$): 204.8 (s), 197.2 (s), 135.8 (s), 133.5 (d), 128.7 (d), 128.5 (d), 56.5 (d), 27.8 (q), 13.4 (q).

EXAMPLE 3

3-methyl-1-phenylpentane-2,4-dione

The procedure described in Example 2 was repeated with ethyl 2-phenylacetate (16.42 g, 100 mmol). The crude product (orange oil, 10.0 g) was distilled first over a 10 cm Vigreux column at 93-103° C./0.06 mbar (5.3 g of a pale yellow oil), then over a 10 cm Widmer column at 94-97° C./0.05 mbar to yield olfactorily pure 3-methyl-1-phenylbutane-2,4-dione (clear, colourless oil, 3.3 g, 17%).

Odor description: honey, buttery, tobacco, dried leaves, honey, jasmone.

$^1$H NMR (400 MHz, $CDCl_3$): (mixture of diketo- and 2 regioisomeric enol forms) 16.48 (s, 0.2H), 7.15-7.41 (m, 5H), 3.71-3.83 (m, 2.6H), 2.14 (s, 0.9H), 2.09 (s, 0.5H), 2.06 (s, 1.6H), 1.89 (s, 1H), 1.42 (s, 1H), 1.32 (d, J=7.1 Hz, 1.7H).

$^{13}$C NMR (101 MHz, $CDCl_3$) (mixture of diketo- and 2 regioisomeric enol forms) 207.6 (s), 206.8 (s), 204.9 (s), 204.5 (s), 191.8 (s), 189.7 (s), 135.2 (s), 133.6 (s), 133.2 (s), 129.6 (d), 129.5 (d), 128.9 (d), 128.7 (d), 128.5 (d), 128.4 (d), 127.2 (d), 126.9 (d), 126.7 (d), 104.7 (s), 59.9 (d), 48.9 (t), 44.9 (t), 42.3 (t), 28.3 (q), 26.2 (q), 23.6 (q), 21.2 (q), 12.8 (q), 12.7 (q).

EXAMPLE 4

3-methyl-6-phenylhexane-2,4-dione

The procedure described in example 2 was repeated with ethyl 3-phenylpropanoate (17.82 g, 100 mmol). The crude product (orange oil, 14.0 g) was distilled first over a 10 cm Vigreux column at 87-105° C./0.06 mbar (10.1 g of an orange oil), then over a 15 cm Widmer column at 116-119° C./0.05 mbar to yield olfactorily pure 3-methyl-6-phenylhexane-2,4-dione (clear, pale yellow oil, 5.2 g, 26%).

Odor description: buttery, floral, black tea, dried leaves, cinnamon.

$^1$H NMR (400 MHz, $CDCl_3$): (mixture of ca. 65% diketo- and 2 regioisomeric enol forms) 7.17-7.34 (m, 5H), 3.65 (q, J=7.1 Hz, 0.6H), 2.88-3.00 (m, 2H), 2.70-2.87 (m, 2H), 2.12 (s, 0.9H), 2.10 (s, 1.8H), 1.97 (s, 0.3H), 1.79 (s, 0.9H), 1.32 (s, 0.6H), 1.30 (d, J=7.1 Hz, 2H).

$^{13}$C NMR (101 MHz, $CDCl_3$): (mixture of ca. 65% diketo- and 2 regioisomeric enol forms) 206.1 (s), 204.8 (s), 192.4 (s), 189.5 (s), 141.0 (s), 140.7 (s), 140.5 (s), 128.4 (d), 128.4 (d), 128.4 (d), 126.1 (d), 126.1 (d), 126.0 (d), 104.5 (s), 61.5 (d), 43.0 (t), 40.1 (t), 37.8 (t), 31.0 (t), 29.7 (t), 29.4 (t), 28.4 (q), 25.9 (q), 23.1 (q), 21.0 (q), 12.4 (q), 12.3 (q).

EXAMPLE 5

3-methyl-6-phenylhex-5-ene-2,4-dione

The procedure described in example 2 was repeated with ethyl cinnamate (17.62 g, 100 mmol). The crude product (orange oil, 11.5 g) was distilled first over a 10 cm Vigreux column at 85-138° C./0.05 mbar (6.6 g of a yellow, slightly turbid oil), then over a 15 cm Widmer column at 116-119° C./0.05 mbar to yield olfactorily pure 3-methyl-6-phenylhex-5-ene-2,4-dione (clear, pale yellow oil, 5.2 g, 26%).

Odor description: floral, buttery, tea, jasmine.

NMR-spectra indicate the presence of 57% enol and 43% diketo form.

$^1$H NMR (400 MHz, $CDCl_3$): 7.67 (br d, J=15.9 Hz, 0.3H), 7.64 (d, J=15.7 Hz, 0.7H), 7.51-7.60 (m, 2H), 7.33-7.44 (m, 3H), 6.96 (dd, J=15.7, 1.3 Hz, 0.6H), 6.82 (d, J=15.9 Hz, 0.3H), 6.47 (d, J=15.7 Hz, 0.1H), 6.45 (d, J=15.9 Hz, 0.02H), 5.66 (s, 0.1H) 4.28 (q, J=7.1 Hz, 0.1H), 3.97 (q, J=7.0 Hz, 0.3H), 2.26 (s, 1.7H), 2.20 (s, 0.9H), 2.18 (s, 0.2H), 2.03 (s, 1.7H), 1.41 (d, J=7.1 Hz, 1.0H).

$^{13}$C NMR (101 MHz, $CDCl_3$): 205.0 (s), 200.4 (s), 196.1 (s), 172.8 (s), 144.6 (d), 139.7 (d), 135.6 (s), 134.0 (s), 130.9 (d), 129.6 (d), 129.0 (d), 128.8 (d), 128.8 (d), 128.6 (d), 127.8 (d), 127.8 (d), 123.8 (d), 119.5 (d), 105.7 (s), 60.2 (d), 28.2 (q), 26.4 (q), 12.8 (q), 12.5 (q).

EXAMPLE 6

1-(4-methoxyphenyl)-2-methylbutane-1,3-dione 6.1. 1-(4-methoxyphenyl)butane-1,3-dione The procedure described in example 1.1. was repeated with methyl 4-methoxybenzoate (16.62 g, 100 mmol). A crystalline byproduct (4-methoxy benzoic acid) was separated from the crude by crystallization in hexane/toluene 4:1 and filtration. The mother liquor was concentrated and the residue purified by flash chromatography on $SiO_2$ (toluene/hexane 1:1 to toluene 100% to toluene/MTBE 9:1) and further by recrystallization from hexane to yield 1-(4-methoxyphenyl)butane-1,3-dione as white crystals (5.15 g, 28%).

Odor description: floral fruity, anisic, saffron.

The NMR-spectra indicate the presence of 71% enol and 29% diketo form.

$^1$H NMR (400 MHz, $CDCl_3$): (enol-H not visible, out of range) 7.91-7.99 (m, 0.3H), 7.85-7.90 (m, 1.7H), 6.92-6.98

(m, 2H), 6.12 (s, 0.8H), 4.06 (s, 0.3H), 3.89 (s, 0.9H), 3.88 (s, 2.1H), 2.30 (s, 1H), 2.18 (s, 3H).

6.2. 1-(4-methoxyphenyl)-2-methylbutane-1,3-dione

The procedure described above for example 1.2. was repeated with 1-(4-methoxyphenyl)butane-1,3-dione (2.0 g, 10.4 mmol). Reaction time at 50° C. was 26 h. Bulb-to-bulb distillation of the crude product at 140-160° C./0.05 mbar yielded the product as a colourless viscous oil (2.05 g, 96%) which was further purified by flash chromatography on $SiO_2$ (toluene/MTBE 29:1) followed by bulb-to-bulb distillation at 160-165° C./0.05 mbar to yield olfactorily pure 1-(4-methoxyphenyl)-2-methylbutane-1,3-dione (1.76 g, 82%) as a semicrystalline colourless oil.

Odor description: buttery, tea, floral.

The NMR-spectra indicate >95% diketo form.

$^1$H NMR (400 MHz, $CDCl_3$): 7.93-8.00 (m, 2H), 6.93-6.99 (m, 2H), 4.43 (q, J=7.1 Hz, 1H), 3.88 (s, 3H), 2.14 (s, 3H), 1.44 (d, J=7.1 Hz, 3H).

$^{13}$C NMR (101 MHz, $CDCl_3$): 205.3 (s), 195.6 (s), 164.0 (s), 131.1 (d), 129.0 (s), 114.0 (d), 56.7 (d), 55.6 (q), 27.7 (q), 13.6 (q).

GC-MS (EI, 70 eV): 206 (3, M$^+$), 163 (3), 107 (6), 92 (8), 77 (10), 64 (4), 43 (6).

EXAMPLE 7

6-(4-methoxyphenyl)-3-methylhexane-2,4-dione

7.1. 6-(4-methoxyphenyl)hexane-2,4-dione

To the suspension of sodium hydride (60% suspension in mineral oil, 2.47 g, 61.7 mmol, 1.1 equiv.) in THF (80 mL) was added the solution of methyl acetate (5.82 g, 78.6 mmol, 1.4 equiv.) in THF (40 mL) at room temperature. The suspension was then heated to 50° C. and the solution of 4-(4-methoxy)-2-butanone (10.0 g, 56.1 mmol, 1.0 equiv) in THF (80 mL) was added dropwise over 45 min. The suspension was then stirred at 60° C. for 24 h, then cooled to RT and poured on 200 mL 2 N aq. HCl-solution. The mixture was extracted twice with 200 mL MTBE and the combined organic layers were washed with water and brine, then dried over $MgSO_4$. The solution was concentrated i. RV and the residue was distilled in a Kugelrohr oven at 160-170° C./0.04 mbar to yield 6-(4-methoxyphenyl)hexane-2,4-dione (10.07 g, 82%) as a slightly yellow oil.

Odor description: odorless.

The NMR-spectra indicate the presence of 80% enol and 20% diketo form.

$^1$H NMR (400 MHz, $CDCl_3$): 15.48 (br s, 0.8H), 7.08-7.15 (m, 2H), 6.81-6.87 (m, 2H), 5.48 (s, 0.8H), 3.79 (s, 2.4H), 3.79 (s, 0.6H), 3.55 (s, 0.4H), 2.92-2.84 (m, 2H), 2.84-2.72 (m, 0.4H), 2.53-2.60 (m, 1.6H), 2.20 (s, 0.6H), 2.05 (s, 2.4H).

$^{13}$C NMR (101 MHz, $CDCl_3$): 203.3 (s), 193.2 (s), 191.1 (s), 158.0 (s), 158.0 (s), 132.7 (s), 132.5 (s), 129.2 (d), 129.16 (d), 113.9 (d), 113.84 (d), 99.98 (d), 58.1 (t, 1 C), 55.2 (q), 45.4 (t), 40.2 (t), 30.8 (d), 30.6 (t), 28.5 (t), 24.8 (q).

GC-MS (EI, 70 eV): 220 (11, M$^+$), 134 (18), 121(100), 91 (6), 85 (9), 108 (3), 77 (5), 43 (14).

7.2. 6-(4-methoxyphenyl)-3-methylhexane-2,4-dione 6-(4-methoxyphenyl)hexane-2,4-dione (36.1 g, 164 mmol) was dissolved in acetone (500 mL) and $K_2CO_3$ (23.8 g, 172 mmol, 1.05 equiv.) was added. The suspension was stirred for 10 min, then iodomethane (34.9 g, 246 mmol, 1.5 equiv.) was added and the mixture stirred for 3 h at 50° C. Additional $K_2CO_3$ (10 g, 72 mmol) and iodomethane (16.0 g, 113 mmol) were added and stirring continued for 18 h at 50° C. The solution was then added to 2 M aqueous HCl-solution (350 mL) and the mixture extracted with MTBE (2×350 mL). The organic layers were washed with brine and dried over $MgSO_4$. The solvent was removed under vacuum and the residue was purified by short-path distillation at 131-136° C./0.05 mbar to yield a brown clear oil (30 g), which was further purified by fine distillation over a 20 cm packed distillation column at 134-138° C./0.06 mbar to yield 6-(4-methoxyphenyl)-3-methylhexane-2,4-dione (24.9 g, 65%) as a colorless oil. The product is ca. 90% pure, the remainder being 6-(4-methoxyphenyl)-3,3-dimethyl hexane-2,4-dione.

Odor description: buttery, fruity, raspberry, liquorice.

The NMR-spectra indicate the presence of keto and enol form in a 2:1 ratio.

$^1$H NMR (400 MHz, $CDCl_3$): (enol-H not visible; out of range); 6.99-7.19 (m, 2H), 6.74-6.88 (m, 2H), 3.79 (s, 0.9H), 3.78 (s, 2.1H), 3.62 (q, J=7.3 Hz, 0.7H), 2.61-2.95 (m, 4H), 2.12 (s, 0.9H), 2.08 (s, 2.1H), 1.77 (s, 0.9H), 1.28 (d, J=7.1 Hz, 2.1H).

$^{13}$C NMR (101 MHz, $CDCl_3$): 206.4 (s), 205.1 (s), 192.5 (s), 189.9 (s), 158.0 (s), 133.1 (s), –132.7 (s), 129.3 (d), 113.9 (d), 104.6 (s), 61.7 (d), 55.2 (q), 43.4 (t), 38.1 (t), 30.3 (t), 28.7 (t), 28.5 (q), 23.3 (q), 12.5 (q).

GC-MS (EI, 70 eV, 6-(4-methoxyphenyl)-3-methyl-hexane-2,4-dione): 234 (11, M$^+$), 163 (12), 134 (45), 121 (100), 91 (9), 77 (7), 43 (23).

GC-MS (EI, 70 eV, 6-(4-methoxyphenyl)-3,3-dimethyl-hexane-2,4-dione): 248 (6, M$^+$), 163 (6), 134 (16), 121 (100), 86 (7), 43 (17).

EXAMPLE 8

6-(4-hydroxyphenyl)-3-methylhexane-2,4-dione

The solution of 6-(4-methoxyphenyl)-3-methylhexane-2,4-dione (as described in Example 7, 16.3 g, 70 mmol) in $CH_2Cl_2$ (150 mL) was cooled to −70° C. and $BBr_3$ (1 M in $CH_2Cl_2$, 100 mL, 100 mmol) was added dropwise over 1.5 h. The solution was then added to 2 M aqueous HCl-solution (250 mL) the phases separated and the aqueous layer further extracted with ethyl acetate (stirring for 30 min). The combined organic layers were washed with brine and dried over $MgSO_4$. The crude product obtained after removal of the solvents was purified by flash chromatography on $SiO_2$ (hexane/MTBE 67:33) followed by bulb-to-bulb distillation at 185° C./0.07 mbar to yield olfactorily pure 6-(4-hydroxyphenyl)-3-methylhexane-2,4-dione (3.32 g, 22%) as an orange oil. The product was 80% pure, the remaining 20% were 6-(4-hydroxyphenyl)-3,3-dimethylhexane-2,4-dione.

Odor description: fruity raspberry, creamy, buttery, sweet powdery, brown sugar.

The NMR-spectra indicate the presence of mainly diketo form.

$^1$H NMR (400 MHz, $CDCl_3$, main product, diketo form): 6.98-7.09 (m, 2H), 6.72-6.80 (m, 2H), 5.82 (br s, 1H), 3.64 (q, J=6.9 Hz, 1H), 2.72-2.90 (m, 4H), 2.09 (s, 3H), 1.29 (d, J=7.1 Hz, 3H).

$^{13}$C NMR (101 MHz, $CDCl_3$, main product, diketo form): 206.9 (s), 205.8 (s), 154.1 (s), 132.4 (s), 129.4 (d), 115.3 (d), 61.6 (d), 43.4 (t), 28.6 (t), 28.5 (q), 12.5 (q).

GC-MS (EI, 70 eV): 220 (8, M+), 205 (1.5), 149 (17), 120(45), 107 (100), 77 (12), 72 (3), 43 (29).

EXAMPLE 9

2-ethyl-1-(p-tolyl)butane-1,3-dione

The procedure described above for example 1.2. was repeated with 1-(p-tolyl)butane-1,3-dione (2.25 g, 12.8 mmol) and ethyl iodide (2.99 g, 19.2 mml). Reaction time was 20 h at 70° C. Purification of the crude by flash chromatography on SiO$_2$ (toluene/MTBE 29:1) followed by bulb-to-bulb distillation at 140° C./0.02 mbar yielded olfactorily pure 2-ethyl-1-(p-tolyl)butane-1,3-dione as a colourless oil (1.30 g, 50%).

Odor description: floral, green, anisic, heliotropin, buttery, tea.

The NMR-spectra indicate >95% diketo form.

$^1$H NMR (400 MHz, CDCl$_3$): 7.86-7.92 (m, 2H), 7.27 (m, 2H), 4.32 (t, J=7.1 Hz, 1H), 2.41 (s, 3H), 2.12 (s, 3H), 1.94-2.10 (m, 2H), 0.94 (t, J=7.3 Hz, 3H).

$^{13}$C NMR (101 MHz, CDCl$_3$): 204.6 (s), 196.0 (s), 144.6 (s), 134.1 (s), 129.5 (d), 128.8 (d), 65.0 (d), 27.7 (q), 22.4 (t), 21.6 (q), 12.1 (q).

GC-MS (EI, 70 eV): 204 (<1, M$^+$), 176 (3), 162 (2), 147 (8), 119 (100), 91 (27), 65 (12), 55 (8), 43 (11).

EXAMPLE 10

1-(4-ethylphenyl)-2-methylbutane-1,3-dione 10.1. 1-(4-ethylphenyl)butane-1,3-dione The procedure described in example 1.1 was repeated with ethyl 4-ethylbenzoate (14.0 g, 79 mmol). A crystalline byproduct (4-methoxy benzoic acid, ca. 30%) was separated from the crude by extraction with saturated aqueous NaHCO$_3$-solution. The crude product was distilled at 93-101° C./0.05 mbar to yield 1-(4-ethylphenyl)butane-1,3-dione (5.47 g, 37%) as a colourless oil.

Odor description: green, acetal, cardboard, saffron.

The NMR-spectra indicate the presence of 90% enol and 10% diketo form.

$^1$H NMR (400 MHz, CDCl$_3$): (enol-H not visible; out of range); 7.86-7.91 (m, 0.2H), 7.80-7.85 (m, 1.8H), 7.26-7.33 (m, 2H), 6.18 (s, 0.9H), 4.09 (br. s, 0.2H), 2.72 (q, J=7.6 Hz, 1.8H), 2.71 (q, J=7.4 Hz, 0.2H), 2.30 (s, 0.3H), 2.20 (s, 2.7H), 1.27 (t, J=7.6 Hz, 3H).

$^{13}$C NMR (101 MHz, CDCl$_3$): (*=diketo form, 10%) 202.4 (s*), 193.4 (s*), 193.0 (s), 183.6 (s), 150.9 (s*), 149.2 (s), 133.9 (s*), 132.3 (s), 129.6 (d*), 128.8 (d*), 128.2 (d*), 128.1 (d), 127.1 (d), 96.3 (d), 54.6 (t), 30.4 (d*), 29.6 (t*), 28.9 (t*)), 28.8 (t), 25.6 (q), 15.1 (q), 15.0 (q*).

GC-MS (EI, 70 eV): 190 (45, M$^+$), 175 (48), 161 (48), 133 (100), 115 (8), 105 (18), 91 (15), 85 (11), 77 (21), 69 (64), 43 (27).

10.2. 1-(4-ethylphenyl)-2-methylbutane-1,3-dione

The procedure described above for example 1.2. was repeated with 1-(4-methoxyphenyl)butane-1,3-dione (2.0 g, 10.4 mmol). Reaction time at 50° C. was 7 h. The crude product was purified by flash chromatography on SiO$_2$ (toluene) followed by bulb-to-bulb distillation at 104° C./0.05 mbar to yield olfactorily pure 1-(4-ethylphenyl)-2-methylbutane-1,3-dione (1.53 g, 32%) as a colourless oil.

Odor description: floral, green, anisic, buttery, tea, mushroom.

The NMR-spectra indicate >95% diketo form.

$^1$H NMR (400 MHz, CDCl$_3$): 7.87-7.93 (m, 2H), 7.28-7.34 (m, 2H), 4.47 (q, J=7.1 Hz, 1H), 2.71 (q, J=7.6 Hz, 2H), 2.15 (s, 3H), 1.44 (d, J=7.1 Hz, 3H), 1.26 (t, J=7.7 Hz, 3H).

$^{13}$C NMR (101 MHz, CDCl$_3$): 205.1 (s), 196.9 (s), 150.8 (s), 133.6 (s), 128.9 (d), 128.3 (d), 56.7 (d), 28.9 (t), 27.8 (q), 15.1 (q), 13.6 (q).

GC-MS (EI, 70 eV): 204 (<1, M$^+$), 162 (2), 105 (11), 77 (10), 43 (9).

EXAMPLE 11

2-methyl-1-(4-(trifluoromethyl)phenyl)butane-1,3-dione 11.1. 1-(4-(trifluoromethyl)phenyl)butane-1,3-dione The procedure described in example 1.1. was repeated with methyl 4-(trifluoromethyl)benzoate (9.0 g, 44.1 mmol). A crystalline byproduct was separated from the crude by crystallization from toluene and filtration. The mother liquor was concentrated and the residue purified by flash chromatography on SiO$_2$ (toluene 100%) and further by recrystallization from hexane/toluene 1:1 to yield 1-(4-(trifluoromethyl)phenyl)butane-1,3-dione (2.8 g, 28%) as an off-white crystalline solid.

Odor description: weak, floral fruity.

The NMR-spectra indicate the presence of 95% enol and 5% diketo form.

$^1$H NMR (400 MHz, CDCl$_3$): 16.0 (s, 0.95H), 7.9-8.0 (m, 2H), 7.7 (d, J=8.1 Hz, 2H), 6.2 (s, 0.95H), 4.1 (s, 0.1H), 2.2 (s, 3H).

$^{13}$C NMR (101 MHz, CDCl$_3$): 195.1 (s), 180.9 (s), 138.1 (s), 133.6 (q, J=33.2 Hz), 127.3 (d), 125.6 (q, J=3.3 Hz), 123.8 (q, J=272.8 Hz), 97.4 (s), 26.2 (q).

GC-MS (EI, 70 eV): 230 (52, M+), 218 (86), 188 (8), 173 (38), 161 (19), 151 (11), 145 (57), 119 (8), 85 (43), 125 (23), 75 (15), 69 (100), 43 (80).

11.2. 2-methyl-1-(4-(trifluoromethyl)phenyl)butane-1,3-dione

The procedure described above for example 1.2. was repeated with 1-(4-methoxyphenyl)butane-1,3-dione (1.6 g, 7.1 mmol). Reaction time at 50° C. was 24 h. The crude product was purified by flash chromatography on SiO$_2$ (toluene/MTBE 19:1) followed by bulb-to-bulb distillation at 120° C./0.02 mbar to yield olfactorily pure 1-(4-ethylphenyl)-2-methylbutane-1,3-dione (1.12 g, 64%) as a white, low-melting solid.

Odor description: buttery, acidic, floral, jasmine, tea.

The NMR-spectra indicate >95% diketo form.

$^1$H NMR (400 MHz, CDCl$_3$): 8.07 (dd, J=8.8, 0.7 Hz, 2H), 7.74 (d, J=8.8 Hz, 2H), 4.49 (q, J=7.1 Hz, 1H), 2.18 (s, 3H), 1.48 (d, J=7.1 Hz, 3H).

$^{13}$C NMR (101 MHz, CDCl$_3$): 204.6 (s), 196.3 (s), 138.6 (s), 134.8 (q, J=33.2 Hz), 129.0 (s), 125.9 (q, J=4.1 Hz), 123.4 (q, J=272.8 Hz), 57.1 (d), 27.8 (q), 13.4 (q).

GC-MS (EI, 70 eV): 244 (2, M+), 225(4), 202 (23), 173 (100), 145 (69), 133 (28), 125 (11), 95 (9), 75 (15), 43 (39).

EXAMPLE 12

2-methyl-1-(p-tolyl)pentane-1,3-dione

To the suspension of potassium t-butoxide (44.8 g, 344 mmol, 1.7 equiv.) in THF (40 mL) was added the solution of 1-(p-tolyl)propan-1-one (30.0 g 202 mmol) in THF (30 mL) at 55° C. over 5 min. Stirring was continued for 1 h at 70° C. (batch temperature) to yield a clear orange solution, to which was added t-butyl propionate (27.3 g, 243 mmol, 1.2 equiv.) within dropwise over 10 min. The resulting solution was stirred at 75° C. for 2 days. The mixture was then diluted with toluene and the solution added to a ice/water mixture. Then 150 mL 2N aq. HCl-solution were added. The phases were separated and the aq. Layer was further extracted with toluene. The combined organic layers were washed with brine and dried over MgSO$_4$.

After evaporation of the solvents, an orange oil was obtained, which was purified by short-path distillation (10 cm Vigreux column) at 52-70° C./0.02 mbar, followed by a fine distillation at 106-119° C./0.02 mbar to yield 2-methyl-1-(p-tolyl)pentane-1,3-dione (15.5 g, 38%) as a colourless oil.

Odor description: floral, tea, buttery.

The NMR-spectra indicate >95% diketo form.

$^1$H NMR (400 MHz, CDCl$_3$): 7.8-7.9 (m, 2H), 7.3-7.3 (m, 2H), 4.5 (q, J=7.1 Hz, 1H), 2.35-2.60 (m, 2H), 2.4 (s, 3H), 1.4 (d, J=6.8 Hz, 3H), 1.0 (t, J=7.2 Hz, 3H).

$^{13}$C NMR (101 MHz, CDCl$_3$): 207.6 (s), 197.0 (s), 144.5 (s), 133.5 (s), 129.5 (d), 128.7 (d), 55.8 (d), 33.9 (t), 21.6 (q), 13.6 (q), 7.7 (q).

GC-MS (EI, 70 eV): 204 (<1, M$^+$), 148 (10), 133 (11), 119 (100), 91 (30), 65 (13), 57 (11).

EXAMPLE 13

1-(benzo[d][1,3]dioxol-5-yl)-2-methylbutane-1,3-dione

The procedure described in Example 12 was repeated with 1-(benzo[d][1,3]dioxol-5-yl)propan-1-one (5.5 g, 30.9 mmol). The crude product was purified by flash chromatography on SiO$_2$ (toluene/MTBE 19:1) followed by bulb-to-bulb distillation at 180° C./0.02 mbar to yield olfactorily pure-(benzo[d][1,3]dioxol-5-yl)-2-methylbutane-1,3-dione (2.52 g, 35%) as a colorless liquid.

Odor description: buttery.

The NMR-spectra indicate >95% diketo form.

$^1$H NMR (400 MHz, CDCl$_3$): 7.56 (dd, J=8.2, 1.9 Hz, 1H), 7.42 (d, J=2.0 Hz, 1H), 6.84 (d, J=8.3 Hz, 1H), 6.05 (s, 2H), 4.27 (q, J=6.9 Hz, 1H), 2.12 (s, 3H), 1.41 (d, J=7.1 Hz, 3H).

$^{13}$C NMR (101 MHz, CDCl$_3$): 205.1, 195.2, 152.3, 148.4, 130.7, 125.2, 108.2, 108.0, 102.0, 56.6, 27.6, 13.7.

COMPARATIVE EXAMPLE 14

2-methyl-1-(m-tolyl)butane-1,3-dione 1-(m-tolyl)butane-1,3-dione was prepared from ethyl 3-methylbenzoate as described in Example 1.1. 1-(m-tolyl)butane-1,3-dione was then monomethylated as described in Example 1.2. The crude product was purified by flash chromatography on SiO$_2$ (toluene/MTBE 39:1) followed by bulb-to-bulb distillation at 150-170° C./0.05 mbar to yield olfactorily pure 2-methyl-1-(m-tolyl)butane-1,3-dione (86%) as a colourless liquid.

Odor description: floral, fruity, rosy, yeast.

The NMR-spectra show >95% keto form.

$^{13}$C NMR (101 MHz, CDCl$_3$): 205.0 (s), 197.5 (s), 138.7 (s), 135.9 (s), 134.4 (d), 129.1 (d), 128.6 (d), 125.8 (d), 56.7 (d), 27.9 (q), 21.3 (q), 13.6 (q).

EXAMPLE 15

Preparation of a precursor (2-methyl-3-(tetradecylamino)-1-(p-tolyl)but-2-en-1-one)

2-methyl-1-(p-tolyl)butane-1,3-dione (product of example 1.2., 3.28 g, 17.3 mmol, 1.0 equiv) and tetradecylamine (3.50 g, 16.4 g, 0.95 equiv.) were dissolved in toluene (30 mL) and p-toluene sulfonic acid was added (0.33 g, 1.73 mmol, 0.1 equiv.). The resulting solution was refluxed for 22 h over a Dean-Stark trap for the continous removal of water. The mixture was quenched with water (80 mL) and the aqueous layer was twice extracted with MTBE. The combined organic layers were washed with water and brine and dried over MgSO$_4$.

After evaporation of the solvents, 2-methyl-3-(tetradecylamino)-1-(p-tolyl)but-2-en-1-one (4.93 g, 74%) was obtained as a viscous yellow liquid. The product consists of a main isomer (>90%) and some minor components.

$^1$H NMR (400 MHz, CDCl$_3$, main isomer): 7.13-7.39 (m, 4H), 3.34 (td, J=7.0, 5.5 Hz, 2H), 2.38 (s, 3H), 2.08 (s, 3H), 1.86 (s, 3H), 1.68 (quin, J=7.3 Hz, 2H), 1.22-1.37 (m, 22H), 0.91 (t, J=7.0 Hz, 3H).

$^{13}$C NMR (101 MHz, CDCl$_3$, main isomer): 192.3 (s), 165.1 (s), 140.5 (s), 138.1 (s), 128.3 (s), 127.1 (s), 97.4 (s), 43.7 (t), 31.9 (t), 30.0 (t), 29.7 (t), 29.6 (t), 29.6 (t), 29.5 (t), 29.3 (t), 27.0 (t), 22.7 (t), 21.3 (q), 16.6 (q), 15.7 (q), 14.1 (q).

GC-MS (EI, 70 eV): 385 (8, M+), 368 (11), 266 (30), 238 (23), 188 (10), 119 (100), 105 (16), 91 (28), 57 (40), 43 (36).

EXAMPLE 16

A Floral Accord for a Feminine Fragrance

| Compound/Ingredients | parts by weight 1/1000 |
|---|---|
| Acetyl Isoeugenol [1] (Crystals) | 5 |
| Benzyl Acetate | 25 |
| Benzyl Salicylate | 140 |
| Cashmeran [2] | 1 |
| Citronellol | 12 |
| Coumarine (Pure Crystals) | 1 |
| Dimethyl Benzyl Carbinyl Acetate | 17 |
| Dimethyl Benzyl Carbinyl Butyrate | 17 |
| Florosa [3] | 50 |
| Galaxolide [4] | 6 |
| Geraniol [5] | 13 |
| Geranium Oil | 6 |
| Hedione [6] | 50 |
| Hexenyl-3-Cis Salicylate | 55 |
| beta - Ionone [7] | 1 |
| Iso E Super [8] | 3 |
| Linalool | 55 |
| Linalyl Acetate | 100 |
| Magnolan [9] | 14 |
| Methyl Anthranilate | 7 |
| Methyl Cedryl Ketone | 180 |
| Muscenone [10] | 7 |
| Nutmeg Oil | 2 |
| Orange Oil | 15 |
| Patchouli Oil Iron free @10% DEP (diethyl phthalate) | 5 |
| Peach Pure [11] | 1 |
| Phenyl Ethyl Alcohol | 75 |
| Prunolide [12] | 1 |
| Vanillin | 13 |
| Dipropylene Glycol (DPG) | 123 |
| Total: | 1000 |

[1] 2-methoxy-4-(prop-1-en-1-yl)phenyl acetate
[2] 1,1,2,3,3-pentamethyl-1,2,3,5,6,7-hexahydro-4H-inden-4-one
[3] 2-isobutyl-4-methyltetrahydro-2H-pyran-4-ol
[4] 4,6,6,7,8,8-hexamethyl-1,3,4,6,7,8-hexahydro-cyclopenta[g]isochromene
[5] (E)-3,7-dimethylocta-2,6-dien-1-ol
[6] methyl 3-oxo-2-pentylcyclopentaneacetate)
[7] 4-(2,6,6-trimethylcyclohex-1-en-1-yl)but-3-en-2-one
[8] 1-(2,3,8,8-tetramethyl-1,2,3,4,5,6,7,8-octahydronaphthalen-2-yl)ethanone
[9] 2,4-dimethyl-4,4a,5,9b-tetrahydroindeno[1,2-d][1,3]dioxine
[10] (Z)-3-methylcyclopentadec-5-enone
[11] 5-heptyldihydrofuran-2(3H)-one
[12] 5-pentyldihydrofuran-2(3H)-one The base accord above for a feminine fine fragrance, dosed at 10 weight % in ethanol (85%, containing 15% water) exhibits a white floral scent with musky and oriental powdery facets. The replacement of 10 parts DPG by 2-methyl-1-(p-tolyl)butane-1,3-dione (Example 1) brings a soft creamy floral impression, which softens the musky and powdery facet, and gives a creamy comfortable feel. The replacement of 10 parts DPG by 2-methyl-1-(p-tolyl)butane-1,3-dione (Example 1) brings a creamy floral gourmand note, reinforcing the white floral "solar" impression.

EXAMPLE 17

Strawberry Fragrance Accord for Shower Gel

| Compound/Ingredients | parts by weight 1/1000 |
|---|---|
| Agrumex [13] | 20 |
| Allyl Caproate | 3 |
| Benzyl Acetate | 5 |
| Benzyl Benzoate | 290 |
| Citronellol | 10 |
| Damascenone [14] @10% TEC | 4 |
| Delta Damascone [15] | 2 |
| Gamma Decalactone [16] | 17 |
| Diethyl Malonate | 3 |
| Dihydro Myrcenol | 40 |
| Dimethyl Benzyl Carbinyl Acetate | 22 |
| Dimethyl Benzyl Carbinyl Butyrate | 23 |
| Ethyl Butyrate | 2 |
| Ethyl Hexanoate | 10 |
| Ethyl Methyl-2-Butyrate | 2 |
| Florosa | 8 |
| Galaxolide | 75 |
| Geranyl Acetate | 5 |
| Hedione | 60 |
| Hexenol-3-Cis | 2 |
| Hexyl Acetate | 15 |
| Hexyl Butyrate | 2 |
| Hexyl Cinnamic Aldehyde [17] | 215 |
| Linalool | 110 |
| Methyl Cinnamate | 5 |
| Orange Oil | 14 |
| Strawberry Pure [18] | 2 |
| Tricyclal [19] | 2 |
| Undecavertol [20] | 2 |
| Dipropylene Glycol (DPG) | 30 |
| | Total: 1000 |

[13] 2-(tert-butyl)cyclohexyl acetate
[14] (E)-1-(2,6,6-trimethylcyclohexa-1,3-dien-1-yl)but-2-en-1-one
[15] (E)-1-(2,6,6-trimethylcyclohex-3-en-1-yl)but-2-en-1-one
[16] 6-pentyltetrahydro-2H-pyran-2-one
[17] (E)-2-benzylideneoctanal
[18] ethyl 3-methyl-3-phenyloxirane-2-carboxylate
[19] 2,4-dimethylcyclohex-3-ene-1-carbaldehyde
[20] (E)-4-methyldec-3-en-5-ol The base accord above dosed at 1 weight % in a shower gel imparts a strawberry impression, with a gourmand and juicy feeling. The replacement of 10 parts DPG by 2-methyl-1-(p-tolyl)butane-1,3-dione (Example 1) softens the top green fruity aspects of this accord, and brings a pleasant creamy impression. The replacement of 30 parts DPG by 2-methyl-1-(p-tolyl)butane-1,3-dione brings a clear creamy gourmand impression with a strawberry yoghurt or strawberry and cream impression.

The invention claimed is:

1. A method of utilizing as fragrance of a compound of formula (I)

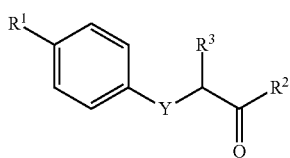

comprising mixing or generating the compound of formula (I) in a fragrance composition or a fragranced article, wherein
$R^1$ is selected from the group consisting of hydrogen, $C_1$-$C_4$ alkyl, hydroxyl, methoxy, $CF_3$ and F;
$R^2$ is selected from the group consisting of methyl and ethyl;
$R^3$ is selected from the group consisting of methyl and ethyl; and
Y is a bivalent residue selected from the group consisting of
—C(O)—; —CH═CH—C(O)—; —$CR^IR^{II}$—C(O)—, wherein $R^I$ and $R^{II}$ are independently selected from hydrogen and methyl; and —$CHR^{III}$—$CHR^{IV}$—C(O)—, wherein $R^{III}$ and $R^{IV}$ are independently selected from hydrogen and methyl with the proviso, that $R^{III}$=$R^{IV}$ are hydrogen or either $R^{III}$ or $R^{IV}$ is methyl.

2. The method according to claim 1 wherein the compound of formula (I) is selected from the group consisting of
2-methyl-1(p-tolyl)butane-1,3-dione,
2-methyl-1-phenylbutane-1,3-dione,
3-methyl-1-phenylbutane-2,4-dione,
3-methyl-6-phenylhexane-2,4-dione,
3-methyl-6-phenylhex-5-ene-2,4-dione,
1-(4-methoxyphenyl)-2-methylbutane-1,3-dione,
6-(4-methoxyphenyl)-3-methylhexane-2,4-dione,
6-(4-hydroxyphenyl)-3-methylhexane-2,4-dione,
2-ethyl-1-(p-tolyl)butane-1,3-dione,
1-(4-ethylphenyl)-2-methylbutane-1,3-dione,
2-methyl-1-(4-(trifluoromethyl)phenyl)butane-1,3-dione, and
2-methyl-1-(p-tolyl)pentane-1,3-dione.

3. A fragrance composition comprising a compound of formula (I)

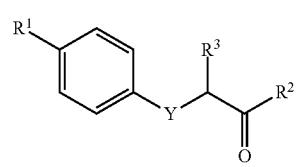

wherein
$R^1$ is selected from the group consisting of hydrogen, $C_1$-$C_4$ alkyl, hydroxyl, methoxy, $CF_3$ and F;
$R^2$ is selected from the group consisting of methyl and ethyl;
$R^3$ is selected from the group consisting of methyl and ethyl; and
Y is a bivalent residue selected from the group consisting of
—C(O)—; —CH═CH—C(O)—; —$CR^IR^{II}$—C(O)—, wherein $R^I$ and $R^{II}$ are independently selected from hydrogen and methyl; and —$CHR^{III}$—$CHR^{IV}$—C(O)—, wherein $R^{III}$ and $R^{IV}$ are independently selected from hydrogen and methyl with the proviso, that $R^{III}$=$R^{IV}$ are hydrogen or either $R^{III}$ or $R^{IV}$ is methyl;
and at least one additional odorant.

4. A fragranced article comprising as odorant a compound of formula (I), or a mixture thereof,

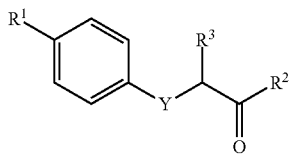

(I)

wherein $R^1$ is selected from the group consisting of hydrogen, $C_1$-$C_4$ alkyl, hydroxyl, methoxy, $CF_3$ and F;

$R^2$ is selected from the group consisting of methyl and ethyl;

$R^3$ is selected from the group consisting of methyl and ethyl; and

Y is a bivalent residue selected from the group consisting of

—C(O)—; —CH=CH—C(O)—; —CR$^I$R$^{II}$—C(O)—, wherein R$^I$ and R$^{II}$ are independently selected from hydrogen and methyl; and —CHR$^{III}$—CHR$^{IV}$—C(O)—, wherein R$^{III}$ and R$^{IV}$ are independently selected from hydrogen and methyl with the proviso, that R$^{III}$=R$^{IV}$ are hydrogen or either R$^{III}$ or R$^{IV}$ is methyl;

and a consumer product base.

5. The fragranced article according to claim 4 wherein the consumer product base is selected from products having a pH of 9 or lower.

6. The fragranced article according to claim 4 selected from shampoo, detergent, fabric conditioner, hair conditioner, liquid soap, bar soap, shower gel, tumble dryer sheet, body lotion, and skin care cream.

7. A method of improving, enhancing or modifying a consumer product base by means of addition thereto of an olfactory acceptable amount of a compound of formula (I)

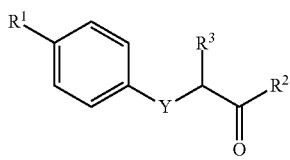

(I)

wherein $R^1$ is selected from the group consisting of hydrogen, $C_1$-$C_4$ alkyl, hydroxyl, methoxy, $CF_3$ and F;

$R^2$ is selected from the group consisting of methyl and ethyl;

$R^3$ is selected from the group consisting of methyl and ethyl; and

Y is a bivalent residue selected from the group consisting of

—C(O)—; —CH=CH—C(O)—; —CR$^I$R$^{II}$—C(O)—, wherein R$^I$ and R$^{II}$ are independently selected from hydrogen and methyl; and —CHR$^{III}$—CHR$^{IV}$—C(O)—, wherein R$^{III}$ and R$^{IV}$ are independently selected from hydrogen and methyl with the proviso, that R$^{III}$=R$^{IV}$ are hydrogen or either R$^{III}$ or R$^{IV}$ is methyl or a precursor thereof.

8. A compound of formula (I)

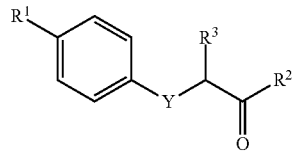

(I)

wherein $R^1$ is selected from the group consisting of hydrogen, $C_1$-$C_4$ alkyl, hydroxyl, methoxy, $CF_3$ and F;

$R^2$ is methyl;

$R^3$ is selected from the group consisting of methyl and ethyl; and

Y is a bivalent residue selected from the group consisting of —CHR$^{III}$—CHR$^{IV}$—C(O)—, wherein R$^{III}$ and R$^{IV}$ are independently selected from hydrogen and methyl with the proviso that R$^{III}$=R$^{IV}$ are hydrogen or either R$^{III}$ or R$^{IV}$ is methyl; 2-ethyl-1-(p-tolyl)butane-1,3-dione, and 2-methyl-1-(p-tolyl)pentane-1,3-dione.

9. A precursor having the formula (II)

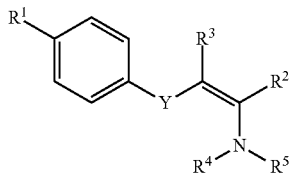

(II)

capable of generating a compound of formula (I),

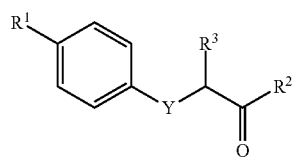

(I)

wherein $R^1$ is selected from the group consisting of hydrogen, $C_1$-$C_4$ alkyl, hydroxyl, methoxy, $CF_3$ and F;

$R^2$ is selected from the group consisting of methyl and ethyl;

$R^3$ is selected from the group consisting of methyl and ethyl;

Y is a bivalent residue selected from the group consisting of

—C(O)—; CH=CH—C(O)—; —CR$^I$R$^{II}$—C(O)—, wherein R$^I$ and R$^{II}$ are independently selected from hydrogen and methyl; and —CHR$^{III}$—CHR$^{IV}$—C(O)—, wherein R$^{III}$ and R$^{IV}$ are independently selected from hydrogen and methyl with the proviso that R$^{III}$=R$^{IV}$ are hydrogen or either R$^{III}$ or R$^{IV}$ is methyl; and wherein $R^4$ and $R^5$, together with the nitrogen atom to which they are attached, form a pyrrolidine or a piperidine ring.

10. The method according to claim 1 comprising admixing to a fragranced article a compound of formula (II)

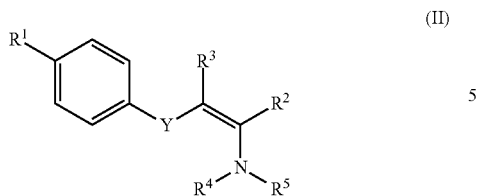

(II)

wherein
$R^4$ and $R^5$ are selected independently from linear or branched $C_1$-$C_{15}$ alkyl, aryl, and $C_3$-$C_8$ cycloalkyl, the cycloalkyl and aryl being optionally substituted with linear or branched $C_1$-$C_7$ alkyl groups; or $R^4$ and $R^5$ may, together with the nitrogen atom to which they are attached, form a 5- or 6-membered ring; or $R^4$ and $R^5$, together with the nitrogen atom to which they are attached, form part of a polymeric entity;

for the in situ generation of a compound of formula (I).

11. The method according to claim 10, wherein $R^4$ and $R^5$, together with the nitrogen atom to which they are attached, form a pyrrolidine or a piperidine ring.

* * * * *